(12) United States Patent
Kinch et al.

(10) Patent No.: US 7,192,698 B1
(45) Date of Patent: Mar. 20, 2007

(54) EPHA2 AS A DIAGNOSTIC TARGET FOR METASTATIC CANCER

(75) Inventors: Michael S. Kinch, Lafayette, IN (US); Nicole D. Zantek, Silver Springs, MD (US)

(73) Assignee: Purdue Research Foundation, West Lafayette, IN (US)

( * ) Notice: Subject to any disclaimer, the term of this patent is extended or adjusted under 35 U.S.C. 154(b) by 976 days.

(21) Appl. No.: 09/640,952

(22) Filed: Aug. 17, 2000

Related U.S. Application Data (60) Provisional application No. 60/149,259, filed on Aug. 17, 1999.

(51) Int. Cl.
*C12Q 1/68* (2006.01)
*G01N 33/00* (2006.01)
*G01N 33/48* (2006.01)
*G01N 33/53* (2006.01)

(52) U.S. Cl. .................. 435/6; 435/7.8; 435/7.92; 435/40.5; 436/64; 436/501; 436/813

(58) Field of Classification Search .............. 435/7.1, 435/4, 6, 7.8, 7.92, 40.5; 436/64, 501, 813
See application file for complete search history.

(56) References Cited

U.S. PATENT DOCUMENTS

| | | | |
|---|---|---|---|
| 4,472,371 A | 9/1984 | Burchiel et al. | |
| 4,704,692 A | 11/1987 | Ladner | |
| 4,816,567 A | 3/1989 | Cabilly et al. | |
| 5,001,225 A | 3/1991 | Taylor | |
| 5,457,048 A * | 10/1995 | Pasquale et al. | |
| 5,514,554 A | 5/1996 | Bacus | |
| 5,585,089 A | 12/1996 | Queen et al. | |
| 5,770,195 A | 6/1998 | Hudziak et al. | |
| 5,811,098 A | 9/1998 | Plowman et al. | |
| 5,824,303 A | 10/1998 | Bartley et al. | |
| 5,872,223 A | 2/1999 | Uckun | |
| 5,876,949 A | 3/1999 | Dreyfuss et al. | |
| 5,981,245 A | 11/1999 | Fox et al. | |
| 6,057,105 A * | 5/2000 | Hoon et al. ............... 435/6 |
| 6,174,670 B1 * | 1/2001 | Wittwer et al. ........... 435/6 |
| 2001/0031252 A1 | 10/2001 | Low et al. | |
| 2001/0031262 A1 | 10/2001 | Low et al. | |
| 2004/0028685 A1 | 2/2004 | Kinch et al. | |
| 2004/0091486 A1 | 5/2004 | Kinch et al. | |

FOREIGN PATENT DOCUMENTS

| | | |
|---|---|---|
| WO | WO 93/00425 | 1/1993 |
| WO | WO 94/04679 | 3/1994 |
| WO | WO 94/29348 | 12/1994 |
| WO | WO 95/15375 | 6/1995 |
| WO | WO 97/15587 * | 5/1997 |
| WO | WO 98/43960 | 10/1998 |
| WO | WO 00/30673 | 6/2000 |
| WO | WO 00/37500 | 6/2000 |
| WO | WO 01/12172 A1 | 2/2001 |
| WO | WO 01/12840 A2 | 2/2001 |
| WO | WO 01/12840 A3 | 2/2001 |
| WO | WO 01/47892 | 7/2001 |
| WO | WO 03/099313 A1 | 12/2003 |
| WO | WO 2004/014292 A2 | 2/2004 |
| WO | WO 94/11020 | 5/2004 |
| WO | WO 03/094859 A2 | 11/2004 |
| WO | PCT/US2004/039112 | 12/2004 |

OTHER PUBLICATIONS

Zanteck, et al., 1998, Mol. Bio. Cell, 9 (Supp):134a, abstract 773, 38th Annual Meeting of the American Society for Cell Biology.*
Kinch, 1998, Hybridoma, vol. 17, No. 3, pp. 227-235.*
Khan et al (American Journal of Clinical Pathology, 1984, vol. 81, pp. 184-191).*
Lindberg et al (Molecular and Cellular biology, 1990, vol. 10, pp. 6316-6324).*
Easty et al (International Journal of Cancer, 1995, vol. 60, pp. 129-136).*
The abstract of Chen et al (Journal of Biological Chemistry, 1998, vol. 273, pp. 24670-24675).*
Larrick et al (In: Human Hybridomas and Monoclonal Antibodies, Engleman and Foung, Ed.s, 1985, pp. 8-9).*
The abstract of Muhlbauer et al (Clinical Cancer Research, May 1999, vol. 5, pp. 1099-1105).*
Easty et al (International Journal of Cancer, 1997, vol. 71, pp. 1061-1065).*
Kerr and Thorpe (LabFax Immunochemistry, 1994, pp. 115, 157, 191-197).*
Campbell (Monoclonal Antibody Technology, 1985, pp. 1-32).*
abstract of Terstappen et al (Vox Sanguinis, 1998, 74 suppl. 2, pp. 269-274).*

(Continued)

*Primary Examiner*—Karen A. Canella
(74) *Attorney, Agent, or Firm*—Mueting, Raasch, Gebhardt, P.A.

(57) ABSTRACT

Method and kits are provided for the detection and diagnosis of metastatic disease. More particularly, the methods and kits employ compounds that can detect EphA2, a specific epithelial cell tyrosine kinase that is overexpressed in metastatic tumor cells. In one embodiment the compound is an antibody capable of binding to an epitope of EphA2.

64 Claims, 2 Drawing Sheets

OTHER PUBLICATIONS

Zelinski et al., "EphA2 Overexpression Causes Tumorigenesis of Mammary Epithelial Cells", *Cancer Research 61*:2301-2306 (Mar. 2001).

Biervert et al. "Semiquantitative expression analysis of ephrine-receptor tyrosine kinase mRNA's in a rat model of traumatic brain injury." *Neurosci Lett.* 2001;315(1-2):25-8.

Blanco et al. "Expression of EphA receptors and ligands during chick cerebellar development." *Mech. Dev.* 2002;114(1-2):225-9.

Bodansky et al., Ed., *Principles of Peptide Synthesis*, Springer-Verlag Inc., NY, 1993, Cover p., Publication p., and Table of Contents.

Bovenkamp et al. "Degenerate PCR-based cloninig method for Eph receptors and analysis of their expression in the developing murine central nervous system and vasculature" *DNA Cell Biol.* 2001;20(4):203-13.

Brantley et al. "Soluble Eph A receptors inhibit tumor angiogenesis and progression in vivo." *Oncogene.* 2002;21(46):7011-26.

Brodeur et al. Mouse-Human Myeloma Partners for the Production of Heterohybridomas, *Monoclonal Antibody Production Techniques and Application* 1987:51-63.

Bruggemann et al., "Designer mice: the production of human antibody repertoires in transgenic animals" *Year Immunol.* 1993;7:33-40.

Carter et al. "EphrinA1 -induced cytoskeletal re-organization requires FAK and p130(cas)." *Nat Cell Biol.* 2002;4(8):565-73.

Cheng et al. "Blockade of EphaA Receptor Tyrosine Kinase Activation Inhibits Vascular Endothelial Cell Growth Factor-Induced Angiogenesis." *Mol Cancer Res.* 2002;1(1):2-11.

Cole et al., Monoclonal Antibodies and Cancer Therapy, Alan R. Liss, 1985, p. 77.

Dohn et al. "Receptor tyrosine kinase EphA2 is regulated by p53-family proteins and induces apoptosis." *Oncogene.* 2001;20(45):6503-15.

Grant, *Synthetic Peptides: A User Guide*, W.H. Freeman and Co., N.Y., 1992, Cover p., Publication p., and Table of Contents only.

Gussow et al. "Humanization of monoclonal antibodies" *Methods Enzymol.* 1991;203:99-121.

Harlow et al., *Antibodies, A Laboratory Manual*, Cold Spring Harbor Publications, New York, 1988.

Hartwell et al. "Integrating Genetic Appraoches into the Discovery of Anticancer Drugs" *Science* 1997;278:1064-1068.

Hess et al., "Molecular regulation of tumor cell vasculogenic mimicry by tyrosine phosphorylation: Role of epithelial cell kinase (ECK/EphA2)," *Cancer Res.*, 2001;61:3250-3255.

Kabat et al., "Sequences of Proteins of Immunological Interest," *National Institutes of Health*, Bethesda, Md. 1987.

Karam et al. "EphA4 is not required for Purkinje cell compartmentation. Brain Res Dev Brain Res." 2002;135(1-2):29-38.

Kinch et al. "Overexpression and functional alterations of the EphA2 tyrosine kinase in cancer" *Clinical & Experimental Metastasis* 2003;20:59-68.

Kinch et al "Predictive Value of the EphA2 Receptor Tyrosine Kinase in Lung Cancer Recurrence and Survival" *Clin Cancer Res.* 2003;9(2):613-8.

Koolpe et al. "An ephrin mimetic peptide that selectively targets the EphA2 receptor." *J Biol Chem.* 2002;277(49):46974-9.

Kratchmarova et al. "Characterization of promoter region and genomic structure of the murine and human genes encoding Src like adapter protein." *Gene.* 2001;262(1-2):267-73.

Lai et al. "Expression of Eph receptors in skeletal muscle and their localization at the neuromuscular junction." *Mol Cell Neurosci.* 2001;17(6):1034-47.

Miao et al., "Activation of EphA2 kinase suppresses integrin function and causes focal-adhesion-kinase dephosphorylation," *Nat. Cell Biol.*, 2000;2(2):62-69.

Miyazaki et al. "EphA2 overexpression correlates with poor prognosis in esophageal squamous cell carcinoma." *Int J Cancer.* 2003;103(5):657-63.

Nakamoto et al. "Diverse roles for the Eph family of receptor tyrosine kinases in carcinogenesis." *Microsc Res Tech.* 2002;59(1):58-67.

Naruse-Nakajima et al. "Involvement of EphA2 in the formation of the tail notochord via interaction with ephrinA1." Mech Dev. 2001;102(1-2):95-105.

NCBI Locus Link Search for "B61" performed Nov. 24, 2003. Http://www.mcbi.nlm.nih.gov/LocusLink/list.cgi.

New England Biolabs Product Catalog, 1996, p. 164.

Nemoto et al., "Overexpression of Protein Tyrosine Kinases in Human Esphageal Cancer," *Pathobiology*, 1997;65:195-203.

Nishida et al. "Domain-specific olivocerebellar projection regulated by the EphA-ephrin-A interaction" *Development.* 2002;129(24):5647-58.

Nowakowski et al. "Structures of the Cancer-Related Aurora-A, FAK, and EphA2 Protein Kinases from Nanovolume Crystallography." *Structure* 2002;10(12):1659-67.

Ogawa et al. "The ephrin-A1 ligand and its receptor, EphA2, are expressed during tumor neovascularization." *Oncogene.* 2000;19(52):6043-52.

Potla et al. "Reduced expression of EphrinA1 (EFNA1) inhibits three-dimensional growth of HT29 colon carcinoma cells." *Cancer Lett.* 2002;175(2):187-95.

Pratt et al. "Activation of the EphA2 tyrosine kinase stimulates the MAP/ERK kinase signaling cascade" *Oncogene.* 2002;21(50):7690-9.

R&D Systems, "Recombinant Mouse Ephrin-A1/Fc Chimera" Catalog No. 602-A1. Apr. 30, 2002.

Rudikoff et al. "Single amino acid substitution altering antigen-binding specificity." *Proc Natl Acad Sci U S A.* 1982;79(6):1979-83.

Studer et al. "Genetic interactions between Hoxa1 and Hoxb1 reveal new roles in regulation of early hindbrain patterning." *Development.* 1998;125(6):1025-36.

Straume et al. "Importance of vascular phenotype by basic fibroblast growth factor, and influence of the angiogenic factors basic fibroblast growth factor/fibroblast growth factor receptor-1 and ephrin-A1/EphA2 on melanoma progression." *Am J Pathol.* 2002;160(3):1009-19.

Vignali et al., "Interactions of CD4 with MHC class II molecules, T cell receptors and p56lck," Phil. Trans. Royal Soc. London, 1993; 342:13-24.

Wang et al. "Negative regulation of EphA2 receptor by Cbl." *Biochem Biophys Res Commun.* 2002;296(1):214-20.

Zantek, "Regulation of EphA2 and Focal Adhesion Kinase in Breast Cancer," Ph.D. thesis, Purdue University; 136 pages. cover date May 1999.

Andres, A. et al., "Expression of two novel *eph*-related receptor protein tyrosine kinases in mammary gland development and carcinogenesis" *Oncogene* 1994; 9:1461-1467.

Easty, D. et al. Protein B61 as an New Growth Factor: Express of B61 and Up-Regulation of Its Receptor Epithelial Cell Kinase during Melanoma Progression *Cancer Research* 1995; 55:2528-2532.

Easty, D. et al., "Novel and Known Protein Tyrosine Kinases and Their Abnormal Expression in Human Melanoma" *J. of Investigative Dermatology* 1993; 101:679-684.

Easty, D. et al., "Protein tyrosine kinases in malignant melanoma" *Melanoma Research* 2000; 10:401-411.

Hein, Patrick W., "Regulation of Cell Signaling Induced by the Cell Adhesion Molecule, E-Cadherin" Ph.D. Thesis, Purdue University; 94 pgs. Cover Date Aug. 1999.

Nemoto et al. "Overexpression of Protein Tyrosine Kinases in Human Esphageal Cancer" *Pathobiology* 1997;65:195-203.

Walker-Daniels et al. "The Mechanism of EphA2 Protein Degradation: Implications of Increased EphA2 Protein Levels in Metastatic Cancer Cells" in the Proceedings of the American Association for Cancer Research Annual Meeting 2001; 42:840.

Zantek, Nicole Dodge "Regulation of EphA2 and Focal Adhesion Kinase in Breast Cancer" Ph.D. thesis, Purdue University; 136 pages. Cover Date May 1999.

P. Agre et al., "The human tumor cloning assay in cancer drug development", *Investigational New Drugs*, 1, 033-045 (1983).

S.-N. Bae et al., "Molecular and cellular analysis of basement membrane invasion by human breast cancer cells in Matrigel-based in vitro assays," Breast Cancer Res. Treat., 24, 241-255 (1993).

T. D. Bartley et al., "B61 is a ligand for the ECK receptor protein-tyrosine kinase," Nature, 368, 558-560 (1994).

J. Baselga et al., "Recombinant Humanized Anti-HER2 Antibody (Herceptin™) Enhances the Antitumor Activity of Paclitaxel and Doxorubicin against HER2/neu Overexpressing Human Breast Cancer Xenografts," Cancer Res., 58, 2825-2831 (1998).

W. Birchmeier, "E-cadherin as a tumor (invasion) suppressor gene", Bioessays, 17 97-99 (1995).

J. Bynum et al., "Development of Class-Switched, Affinity-Matured Monoclonal Antibodies Following a 7-Day Immunization Schedule", Hybridoma, 18 407-411 (Oct. 1999).

W. G. Cance et al., "Protein kinases in human breast cancer", Breast Cancer Research and Treatment, 35, 105-114 (1995).

G. J. Clark et al., "Overexpression of the Ras-related TC21/R-Ras2 protein may contribute to the development of human breast cancers," Oncogene, 12, 169-176 (1996).

S. Davis et al., "Ligands for EPH-related receptor tyrosine kinases that require membrane attachment or clustering for activity," Science, 266, 816-819 (1994).

V. T. DeVita, Jr., "Principles of Cancer Management: Chemotherapy", Cancer: Principles and Practice of Oncology, Fifth Edition, V. T. Devita Jr. et al., Eds., Lippincott-Raven, Philadelphia, 333-347 (1997).

R. B. Dickson et al., "Growth factors in breast cancer," Endocrine Rev., 16, 559-589 (1995).

D. J. Easty et al., "Abnormal protein tyrosine kinase gene expression during melanoma progression and metastasis," Intl. J. Cancer, 60, 129-136 (1995).

Eph Nomenclature Committee, "Unified Nomenclature for Eph Family Receptors and Their Ligands, the Ephrins", Cell, 90, 403-404, (1997).

I. J. Fidler, "Molecular Biology of Cancer: Invasion and Metastasis", In Cancer: Principles and Practice of Oncology, V. T. Devita et al, eds. (Philadelphia: Lippincott-Raven), p. 135-152 (1997).

S. M. Frisch, "Integrins and anoikis", Current Opinion in Cell Biology, 9, 701-706 (1997).

D. W. Fry et al., "Inhibitors of protein tyrosine kinases", Current Opinion in Biotechnology, 6, 662-667 (1995).

N. W. Gale et al., "Ephrins and their receptros: a repulsive topic?", Cell Tissue Res., 290, 227-241 (1997).

D. Giunciuglio et al., "Invasive phenotype of MCF10A cells overexpressing c-Ha-ras and c-erb-2 oncogenes," Intl. J. Cancer, 63, 815-822 (1995).

J. R. Glenney, Jr. et al., "Novel Tyrosine Kinase Substrates from Rous Sarcoma Virus-transformed Cells are Present in the Membrane Skeleton", The Journal of Cell Biology, 108, 2401-2408 (1989).

A. W. Hamburger, "The Human Tumor Clonogenic Assay as a Model System in Cell Biology", International Journal of Cell Cloning, 5, 89-107 (1987).

D. Hanahan et al., "The hallmarks of cancer", Cell, 100 57-70 (Jan. 7, 2000).

D. E. Henson, "Molecular and genetic targets in early detection", Current Opinion in Oncology, 11, 419-425 (1999).

S. J. Holland et al., Cell-contact-dependent signalling in axon growth and guidance: Eph receptor tyrosine kinases and receptor protein tyrosine phosphatase beta. Curr Opinion Neurobiol., 8 117-127 (1998).

R. M. Hudziak et al., "p185$^{HER2}$ Monoclonal Antibody Has Antiproliferative Effects In Vitro and Sensitizes Human Breast Tumor Cells to Tumor Necrosis Factor," Mol. Cell Biol., 9, 1165-1172 (1989).

J. Huai et al., "Investigation of a Possible Receptor Function of Ephrina Ligands", European Journal of Neuroscience, 12, 179 (Sep. 2000).

T. Hunter, "Oncoprotein networks", Cell, 88 333-346 (1997).

S. B. Kanner et al., "Monoclonal antibodies to individual tyrosine-phosphorylated protein substrates of oncogene-encoded tyrosine kinases", Proc. Natl. Acad. Sci. USA, 87, 3328-3332, (May 1990).

P. Keely et al. "Integrins and GTPases in tumour cell growth, motility and invasion", Trends Cell Biol., 8 101-106 (1998).

K. Kilpatrick et al., "Gene Gun Delivered DNA-Based Immunizations Mediate Rapid Production of Murine Monoclonal Antibodies to the Flt-3 Receptor", Hybridoma, 17, 569-576 (1998).

K. Kilpatrick et al., "High Affinity Monoclonal Antibodies to PED/PEA-15-Generated Using 5 µg of DNA", Hybridoma, 19, 297-302 (Aug. 2000).

K. Kilpatrick et al., "Rapid Development of Affinity Matured Monoclonal Antibodies Using RIMMS," Hybridoma, 16, 381-389 (1997).

M. S. Kinch et al., "Identification of Tyrosine Phosphorylated Adhesion Proteins in Human Cancer Cells," Hybridoma, 17, 227-235 (1998).

M. S. Kinch et al., "Tyrosine phosphorylation regulates the adhesions of ras-transformed breast epithelia," J. Cell Biol., 130, 461-471 (1995).

B. S. Kondapaka et al., "Tyrosine kinase inhibitor as a novel signal transduction and antiproliferative agent: prostate cancer", Molecular and Cellular Endocrinology, 117, 53-58 (1996).

J. A. Lawrence, "Mechanisms of tumor invasion and metastasis", World J. Urol., 14, 124-130 (1996).

A. Levitzki, "Tyrosine Kinase Inhibition: An Approach to Drug Development", Science, 267, 1782-1788 (1995).

G. D. Lewis et al., "Differential responses of human tumor cell lines to anti-p185$^{HER2}$ monoclonal antibodies," Cancer Immunol. Immunother., 37, 255-263 (1993).

R. Lindberg et al., "cDNA Cloning and Characterization of Eck, an Epithelial Cell Receptor Protein-tyrosine Kinase in the Eph/elk Family of Protein Kinases," Mol. Cell Biol., 10(12):6316-6324 (Dec. 1990).

R. K. Malik et al., "Integrin-mediated signaling in normal and malignant cells: a role of protein tyrosine kinases", Biochimica et Biophysica Acta, 1287, 73-76 (1996).

H. Miao et al., "Activation of EphA2 kinase suppresses integrin function and causes focal-adhesion-kinase dephosphorylation," Nat. Cell Biol., 2(2):62-69 (Feb. 2000).

F. R. Miller et al., "Xenograft model of progressive human proliferative breast disease", J. Natl Cancer Instit., 85, 1725-1732 (1993).

M. Nakamoto, "Eph receptors and ephrins", Int'l Biochem. Cell Biol., 32, 7-12 (2000).

H. F. Oettgen et al., "The History of Cancer Immunotherapy," in Biologic Therapy of Cancer, Devita et al., eds., Lippincott, Philadelphia, Chapter 6, pp. 87-119 (1991).

A. Pandey et al., "Activation of the Eck receptor protein tyrosine kinase stimulates phosphatidylinositol 3-kinase activity," J. Biol. Chem., 269, 30154-30157 (1994).

A. Pandey et al., "Characterization of a novel src-like adapter protein that associates with the Eck receptor tyrosine kinase," J. Biol. Chem., 270, 19201-19204 (1995).

J. T. Parsons et al., "Protein-tyrosine kinases, oncogenes, and cancer", Important Adv. Oncol., 3-17 (1993).

E. B. Pasquale, "The Eph family of receptors", Current Opinion in Cell Biology, 9, 608-615 (1997).

R. Patarca "Protein Phosphorylation and Dephosphorylation in Physiologic and Oncologic Processes", Critical Reviews in Oncogenesis, 7, 343-432 (1996).

R. J. Pauley et al., "The MCF10 family of spontaneously immortalized human breast epithelial cell lines: models of neoplastic progression", Eur J. Cancer Prev 2 Suppl, 3 67-76 (1993).

Pegram et al., Abstract, "Antibody dependent cell-mediated cytotoxicity in breast cancer patients in Phase III clinical trials of a humanized anti-HER2 antibody," Proc. Am. Assoc. Cancer Res., 38, 602 (1997).

M. D. Pegram et al., "HER-2/neu as a predictive marker of response to breast cancer therapy," Breast Cancer Res. Treat., 52, 65-77 (1998).

M. F. Press et al., "HER-2/neu Oncogene Amplification and Expression in Breast and Ovarian Cancers," Prog. Clin. & Biol. Res., 354A, 209-221 (1990).

J. E. Price, "Analysing the metastatic phenotype", J. Cell Biochem., 56 16-22 (1994).

J. E. Price, "Metastasis from human breast cancer cell lines", *Breast Cancer Res. Treat.*, 39 93-102 (1996).

J. S. Rhim et al., "Human Prostate Carcinogenesis," *Crit. Rev. Oncog.*, 8, 305-328 (1997).

S. Roche et al., "Src-like adaptor protein (SLAP) is a negative regulator of mitogenesis", *Current Biol.*, 8 975-978 (1998).

I. M. Rosenberg et al., "Epithelial cell kinase-B61: an autocrine loop modulating intestinal epithelial migration and barrier function," *Am. J. Physiol.*, 273, G824-G832 (1997).

S. A. Rosenberg, "Principles of Cancer Management: Surgical Oncology", *Cancer: Principles and Practice of Oncology, Fifth Edition*, V. T. Devita, Jr. et al., Eds., Lippincott-Raven, Philadelphia, cover page, table of contents and 295-333 (1997).

E. Ruoslahti, "Cell adhesion and tumor metastasis", *Princess Takamatsu Symp*, 24 99-105 (1994).

E. Ruoslahti, "Fibronectin and Its Integrin Receptors in Cancer" *Advances in Cancer Research*, 76, 1-20 (1999).

M. F. Sarosdy et al., "Prediction of Response to Cancer Chemotherapy", *Drugs*, 26, 454-459 (1983).

D. D. Schlaepfer et al., "Signal transduction from the extracellular matrix-a role for the focal adhesion protein-tyrosine kinase FAK", *Cell Structure Function*, 21 445-450 (1996).

S. Shak, "Overview of the trastuzumab (Herceptin) anti-HER2 monoclonal antibody clinical program in HER2-overexpressing metastatic breast cancer," *Seminars Oncol.*, 26, 71-77 (Aug. 1999).

D. J. Slamon et al., "Studies of the HER-2/neu Proto-oncogene in Human Breast and Ovarian Cancer," *Science*, 244, 707-712 (1989).

P. S. Steeg et al. "Molecular analysis of premalignant and carcinoma in situ lesions of the human breast", *Am J Pathology*, 149 733-738 (1996).

P. van der Geer et al., "Receptor Protein-Tyrosine Kinases And Their Signal Transduction Pathways," *Annu. Rev. Cell Biol.*, 10, 251-337 (1994).

H. D. Varmus et al., "Biochemical mechanisms of oncogene activity: proteins encoded by oncogenes", *Cancer Surv.*, 5 153-158 (1986).

T. Volberg et al., "The effect of tyrosine-specific protein phosphorylation on the assembly of adherens-type junctions," *EMBO J.*, 11, 1733-1742 (1992).

J. Walker-Daniels et al., "Overexpression of the EphA2 Tyrosine Kinase in Prostate Cancer," *Prostate*, 41(4):275-280 (Dec. 1999).

D. J. Waters et al., "Spontaneous Metastasis of PC-3 Cells in Athymic Mice After Implantation in Orthotopic or Ectopic Microenvironments," *Prostate*, 26, 227-234 (1995).

V. M. Weaver et al., "The development of a functionally relevant cell culture model of progressive human breast cancer," *Semin. Cancer Biol.*, 6, 175-184 (1995).

L. M. Weiner, "Monoclonal antibody therapy of cancer," *Seminars Oncol.*, 26, 43-51 (Oct. 1999).

N. D. Zantek et al., Abstract "Identification of an Adhesion-Associated Tyrosine Kinase that is Tightly Regulated In Breast Cancer," American Society for Cell Biology, (Dec. 15, 1998).

N. D. Zantek et al., "E-Cadherin Regulates the Function of the EphA2 Receptor Tyrosine Kinase," *Cell Growth Differ.*, 10(9):629-638 (Sep. 1999).

N. D. Zantek et al., "Identification of an adhesion-associated tyrosine kinase that is tightly regulated in breast cancer," *Mol. Bio. Cell*, 8(Supp):134A, abstract 777 (1997); 37th Annual Meeting of the American Society for Cell Biology, (Dec. 13-17, 1997).

N. D. Zantek et al., "Epithelial cell kinase (ECK/EPHA2) regulation in breast cancer," *Mol. Bio. Cell*, 9(Supp):134a, abstract 773 (1998); 38th Annual Meeting of the American Society for Cell Biology, (Dec. 12-16, 1998).

N. D. Zantek et al., "Regulation of the EphA2 receptor tyrosine kinase by estrogen and myc," *Proceedings of the American Assoc. for Cancer Research Annual*, 40:687, abstract 4537 (1999); 90th Annual Meeting of the American Association for Cancer, (Apr. 10-14, 1999).

Walker-Daniels et al., "Overexpression of EphA2 in Metastatic Cancer Cells: A Role for Ras Signaling," Abstract 2469, *Molecular Biology of the Cell(Supplement)*, 10:427a (Nov. 1999); 39th Annual Meeting of the American Society for Cell Biology, Washington, DC (Dec. 11-15, 1999).

Zantek et al., "Chapter 25: Analysis of Cell Migration," In: *Methods in Cell Biology, vol. 63, Cytometry, Third Edition, Part A*, Darzynkiewicz et al., eds., Academic Press, San Diego, CA, USA, Title page, publication page, and pp. 549-559 (2001).

U.S. Appl. No. 09/952,560, filed Sep. 12, 2001, Kilpatrick et al.

U.S. Appl. No. 11/004,005, filed Dec. 2, 2001, Kilpatrick et al.

U.S. Appl. No. 10/994,129, filed Nov. 19, 2004, Kinch et al.

Aasheim et al. "A splice variant of human ephrin-A4 encodes a soluble molecule that is secreted by activated human B lymphocytes." *Blood*. 2000;95(1):221-30.

Abrahmsen et al., "Engineering Subtilisin and Its Substrates for Efficient Ligation of Peptide Bonds in Aqueous Solution," *Biochemistry*, 1991;30:4151-4159.

Angrist et al. Chromosomal Localization of the Mouse Src-like Adapter Protein (Slap) Gene and Its putative Human Homolog SLA, *Genomics* 1995;30:623-625.

Baggiolini et al., "Interleukin-8, a chemotactic and inflammatory cytokine," *FEBS Lett.*, 1992; 307(1):97-101.

Baggliolini et al. "Interleukin-8 and the Chemokine Family" *Int. J. Immunopharmae* 1995;17(2):103-108.

Behrens et al., "Cell-cell adhesion in invasion and metastasis of carcinomas," *Cancer Treat. Res.*, 1994; 71:251-266.

Boerner et al. "Production of antigen-Specific Human Monoclonal Antibodies from in vitro-primed Human Splenocytes", *J. Immunol.*, 1991; 147(1):86-95.

Bohme et al. "PCR mediated detection of a new human receptor-tyrosine-kinase, HEK 2." *Oncogene*. 1993;8(10):2857-62.

Bowie et al. "Deciphering the Message in Protein Sequences: Tolerance to Amino Acid Substitutions" *Science* 247:1306-1310.

Brady-Kalnay et al., "Dynamic Interaction of PTPμ with Multiple Cadherins In Vivo" *J. Cell Biol.*, 1998; 141:287-296.

Burgess et al. "Possible Dissociation of the Heparin-binding Mitogenic Activities of Heparin-binding (Acidic Fibroblast) Growth Factor-1 from Its Receptor-binding Activities by Site-directed Mutagensis of a Single Lysine Residue" *J. Cell Biology* 1990;111:2129-2138.

Burridge et al., "Focal adhesions: transmembrane junctions between the extracellular matrix and the cytoskeleton," *Annu. Rev. Cell Dev. Biol.*, 1988; 4:487-525.

Burridge et al., "Focal adhesions, contractility, and signaling," *Annu. Rev. Cell Dev. Biol.*, 1996; 12:463-518.

Carles-Kinch "Antibody Targeting of the EphA2 Tyrosine Kinase Inhibits Malignant Cell Behavior," *Cancer Research* 2002;62:2840-2847.

Carter et al., "Humanization of an anti-p185$^{HER2}$ antibody for human cancer therapy," *Proc. Natl. Acad. Sci. USA*, 1992;89:4285-4289.

Chen et al. "An enhancer element in the EphA2 (Eck) gene sufficient for rhombomere-specific expression is activated by HOXA1 and HOXB1 homeobox proteins." *J Biol Chem.* 1998;273(38):24670-5.

Chen et al. "Germ-line inactivation of the murine Eck receptor tyrosine kinase by gene trap retroviral insertion." *Oncogene* 1996;12(5):979-88.

Chen et al., "Integrin-mediated cell adhesion activates mitogen-activated protein kinases," *J. Biol. Chem.*, 1994;269:26002-26005.

Chothia et al., "Canonical Structures for the Hypervariable Regions of Immunoglobulins," *J. Mol. Biol.*, 1987;196:901-917.

Clark et al. "Aberrant function of the Ras signal transduction pathway in human breast cancer" *Breast Cancer Res. Treat.* 1995;35(1):133-144.

Clark et al., "The Ras-related protein Fheb is farnesylated and antagonizes Ras signaling and transformation," *J. Biol. Chem.*, 1997; 272:10608-10615.

Clark-Lewis et al. Chemical Synthesis, Purification, and Characterization of Two Inflammatory Proteins, Neutrophil Activating Peptide 1 (Interleukin-8) and Neutrophil Activating Peptide 2, *Biochemistry* 1991;30:3128-3135.

Clark-Lewis et al. Structural Requirements for Interleukin-8 Function Identified by Design of Analogs and CXC Chemokine Hybrids, *J. Biol. Chem*, 1994;269:16075-16081.

Connor et al. "Expression and tyrosine phosphorylation of Eph receptors suggest multiple mechanisms in patterning of the visual system." *Dev Biol.* 1998;193(1):21-35.

Curti "Physical barriers to drug delivery in tumors" Critical Reviews in Oncology/Hematology1993;14:29-39.

D'Amico "Predicting the Sites of Metastasis Form Lung Cancer Using Molecular Biologic Markets" *Ann. Throac. Surg.* 2001;72:1144-8.

Dawson et al., "Synthesis of Proteins by Native Chemical Ligation," *Science*, 1994;266:776-779.

deLisle et al., *Techniques in Protein Chemistry IV*, Academic Press, New York, 1992, pp. 257-267.

Dermer "Another Anniversary for the War on Cancer" Bio/Technology 1994;12:320.

Easty et al. "Up-regulation of ephrin-A1 during melanoma progression." *Int J Cancer.* 1999;84(5):494-501.

Fenrick "TEL, a Putative Tumor Suppressor, Modulates Cell Growth and Cell Morphology of Ras-Transformed Cells While Repressing the Transcription of *stromelysin-1*" Molecular and Cellular Biology 2000;20(6):5828-5839.

Ferrone et al., eds., *Handbook of Monoclonal Antibodies*, Noges Publications, Park Ridge, N.J., 1985. Chapter 22 and 303-357.

Foulkes et al. Purification and characterization of a protein-tyrosine kinase encoded by the Abelson murine leukemia virus *J. Biol. Chem.* 1985; 260:8070-8077.

Freshney *Culture of Animal Cells. A Manual of Basic Technique* 1983;3-4.

Gale et al., "Eph receptors and ligands comprise two major specificity subclasses and are reciprocally compartmentalized during embryogenesis," *Neuron*, 1996;17:9-19.

Ganju et al. "The Eck receptor tyrosine kinase is implicated in pattern formation during gastrulation, hindbrain segmentation and limb development." *Oncogene.* 1994;9(6):1613-24.

Geiger et al., "Cadherins," *Annu. Rev. Cell Biol.*, 1992;8:307-332.

George et al., "The VAB-1 Eph receptor tyrosine kinase functions in neural and epithelial morphogenesis in C. Elegans," *Cell*, 1998; 92:633-643.

Goding, *Monoclonal Antibodies: Principles and Practice*, Academic Press, 1986, cover page and pp. 59-103.

Gura Systems for Identifying New Drugs are Often Faulty *Science* 1997;278:1041-1042.

Helbling et al. "Requirement for EphA receptor signaling in the segregation of Xenopus third and fourth arch neural crest cells." *Mech Dev.* 1998;78(1-2):63-79.

Henkeneyer et al., "Nuk controls pathfinding of commissural axons in the mammalian central nervous system," *Cell*, 1996; 86:35-46.

Hoogenboom et al.,:By-passing Immunisation Human Antibodies from Syntheti Repertoires of Germline $V_H$ Gene Segments Rearranged *in Vitro J. Mol. Biol.*, 1991;227:381-388.

Hunter et al. "Novel receptor protein-tyrosine kinases" *Adv Second Messenger Phosphoprotein Res.* 1990;24:260-5.

Hunter et al. "Receptor protein tyrosine kinases and phosphatases." Cold Spring Harb Symp Quant Biol. 1992;57:25-41.

Hutchcroft, "B lymphocyte activation is accompanied by phosphorylation of a 72-kDa protein-tyrosine kinase," *J. Biol. Chem.*, 1991;266:2595-14849.

Jain "Barriers to Drug Delivery in Solid Tumors" *Scientific American*, 1994;58-65.

Jakobovits et al., "Analysis of homozygous mutant chemeric mice: Delection of the immunoglobulin heav-chain joining region blocks B-cell development and antibody production" *Proc. Natl. Acad. Sci. USA*, 1993; 90:2551-2555.

Jakobovits et al., "Germ-like transmission and expression of a human-derived yeast artificial chromosome" *Nature*, 1993;362:255-258.

Jones, "Replacing the complementarity-determining regions in a human antibody with those from a mouse" *Nature* 1986;321:522-525.

Khosravi-Far et al. "Activation of Rac1, RhoA, and Mitogen-Activated Protein Kinases Is Required for Ras Transformation" *Molecular and Cellular Biology* 1995;15(11)6443-6453.

Kikawa et al. "Regulation of the EphA2 kinase by the low molecular weight tyrosine phosphatase induces transformation." *J Biol Chem.* 2002;277(42):39274-9.

Kinch et al., "Altered adhesions in ras-transformed breast epitheilal cells," *Biochem. Soc. Trans.*, 1995;23:446-450.

Kinch et al., "Cell adhesion mediated by CD4 and MHC class II proteins requires active cellular processes," *J. Immunol.*, 1993; 151:4552-4561.

Kinch et al., "Cytometric analysis of cell contact and adhesion," *Cytometry*, Darzynkiewicz et al., Eds., 3$^{rd}$ Ed. Academic Press, San Diego, CA, 2000.

Kinch et al. "E-cadherin engagement stimulates tyrosine phosphorylation" *Cell Adhes. Commun.* 1997;4:425-437.

Kinch et al., "The protein tyrosine kinase p56$^{lck}$ regulates cell adhesion mediated by CD4 and MHC class II proteins," *J. Exp Med.*, 1994; 180:1729-1739.

Kirk et al., "The human anti-porcine cell mediated response: In vitro studies of function and molecular interaction," *Transplant*, 1993; 55(4):924-931.

Kohler et al. "Continous culture of fused cels secreting antibody of predefined specificity" *Nature* 1975;256:495-497.

Kozbor et al., "A Human Hybrid Myeloma for Production of Human Monoclonal Antibodies," *J. Immunol.*, 1984; 133:3001-3005.

Lazar et al. "Transforming Growth Factor : Mutation of Aspartic Acid 47 and Leucine 48 Results in Different Biological Activities" *Molecular and Cellular Biology* 1998;8(3):1247-1252.

Lickliter et al. "Embryonic stem cells express multiple Eph-subfamily receptor tyrosine kinases." *Proc Natl Acad Sci U S A.* 1996;93(1):145-50.

Marks et al. "By-passing immunization. Human antibodies from V-gene libraries displayed on phage." *J Mol Biol.* 1991;222(3):581-97.

Maru et al., "Overexpression confers an oncogenic potential upon the *eph* gene," *Oncogene*, 1990;5:445-447.

McLaughlin "Functional consequences of coincident expression of EphA receptors and ephrin-A ligands." *Neuron.* 1999;22(4):636-9.

Michael et al. "Efficient gene-specific expression of cre recombinase in the mouse embryo by targeted insertion of a novel IRES-Cre cassette into endogenous loci." *Mech Dev.* 1999;85(1-2):35-47.

Miller et al., "The engagement of $\beta_1$ integrins on promonocytic cells promotes phosphorylation of Syk and formation of a protein complex containing Lyn and $\beta_1$ integrin," *Eur. J. Immuno.*, 1999;29:1426-1434.

Morrison et al., "Chimeric human antibody molecules: Mouse antigen-binding domains with human constant region domains," *Proc. Natl. Acad. Sci. USA*, 1984;81:6851-6855.

Munson et al., "LIGAND: A Versatile Computerized Approach for Characterization of Ligand-Binding Systems," *Anal. Biochem.*, 1980;107:220-239.

Murphy et al., "Epidermal growth factor gene expression in human breast cancer cells: regulation of expression by progestins," *Cancer Res.*, 1988; 48:4555-4560.

Nose et al., "Expressed recombinant cadherins medlatd cell sorting in model systems," *Cell*, 1988;54:993-1001.

O'Brien et al., "A mechanism for trabecular meshwork cell retraction: Ethacrynic acid initiates the dephosphorylation of focal adhesion proteins," *Exp. Eye Res.*, 1997;65:471-483.

Orsulic et al. "Expression of Eph receptors and ephrins is differentially regulated by E-cadherin." *J Cell Sci.* 2000;113(Pt 10):1793-802.

Oslo et al., *Remington's Pharmaceutical Science*, 16$^{th}$ ed., Mack Publishing Co., 1980: Table of Contents and Cover Page.

Owens et al., "Overexpression of focal adhesion kinase (p125$^{FAK}$) in invasive human tumors," *Cancer Res.*, 1995;55:2752-2755.

Ozawa et al., "A possible new adhesive site in the cell-adhesion molecule uvomorulin," *Mech. Dev.*, 1991;33:49-56.

Paine et al., "Characterization of ephithelial phenotypes in mortal and immortal human breast cells," *Int. J. Cancer*, 1992;50:463-473.

Pandey et al., "Role of B61, the ligand for the Eck receptor tyrosine kinase, in TNF-α-induced angiogeneis," *Science*, 1995; 269:567-569.

Parsons, "Integrin-mediated signaling: regulation by protein tyrosine kinases and small GTP-binding proteins," *Curr. Opin. Cell Biol.*, 1996;8: 146-152.

Patarca "Protein Phosphorylation and Dephosphorylation in Physiologic and Oncologic Processes", *Critical Reviews™ in Oncogenesis*, 1996;7:343-432.

Presta "Antibody engineering" *Current Op. Struct. Biol.* 1992;2:593-596.

Presta et al., "Humanization of an Antibody Directed Against IgE," *J. Immunol.*, 1993;151:2623.

Rajarathnam et al., "H NMR Studies of Interleukin 8 Analogs: Characterization of the Domains Essential for Functions," *Biochemistry*, 1994; 33:6623-30.

Riechmann et al., "Reshaping human antibodies for therapy," *Nature*, 1988; 332:323-327.

Rosenberg, "Principles of Cancer Management: Surgical Oncology", *Cancer: Principles and Practice of Oncology, Fifth Edition*, V. T. Devita, Jr. et al., Eds., Lippincott-Raven, Philadelphia, 1997:cover page, table of contents and 295-333.

Ruiz et al. "The expression of the receptor-protein tyrosine kinase gene, eck, is highly restricted during early mouse development." *Mech Dev.* 1994;46(2):87-100.

Schnolzer et al., "Constructing Proteins by Dovetailing Unprotected Synthetic Peptides: Backbone-Engineered HIV Protease," *Science*, 1992;256:221-225.

Sims et al. "A Humanized CD18 Antibody Can Bock Funciton without Cell Destruction" *J. Immunol.* 1993;151:2296.

Sliwkowski et al., "Nonclinical Studies Addressing the Mechanism of Action of Trastuzumab (Herceptin)" *Seminars in Oncology*, 1999; 26:60-70.

Smith et al. "Cardiac Glycoside-Specific Antibodies in the Treatment of Digitalis Intoxication" *Antibodies in Human Diagnosis and Therapy* 1977:365-389.

Southern et al., "Transformation of mammalian cells to antibiotic resistance with a bacterial gene under control of the SV40 early region promoter," *J. Mol. Appl. Genet.*, 1982;1:327-341.

Stearns et al., "Human xenograft models for prostate cancer," The Prostate, 1998; 36:56-58.

Stein et al. "Eph receptors discriminate specific ligand oligomers to determine alternative signaling complexes, attachment, and assembly responses." *Genes Dev.* Mar. 1, 1998;12(5):667-78.

Stein et al. Nck recruitment to Eh receptor, EphB1/ELK couples ligand activation to c-JUN kinase, *J. Biol. Chem.* 1998;273:1303-1308.

Sulman et al. "ECK, a human EPH-related gene, maps to 1p36.1, a common region of alteration in human cancers." *Genomics* 1997;40(2):371-4.

Verhoeyen et al., "Reshaping Human Antibodies: Grafting an Antilysozyme Activity," *Science*, 1988;239:1534-1536.

Vestweber et al., "Identification of a putative cell adhesion domain of uvomorulin," *EMBO J.*, 1985;4:3393-3398.

Vestweber et al., "Rabbit antiserum against a purified surface glycoprotein decompacts mouse preimplanted embryos and reacts with specific adult tissues," *Exp. Cell Res.*, 1984;152:169-178.

Vestweber et al., "Some structural and functional aspects of the cell adhesion molecule uvomorulin," *Cell Differ.*, 1984;15:269-273.

Walker-Daniels et al. "c-Cbl-Dependent EphA2 Protein Degradation Is Induced by Ligand Binding" *Mol Cancer Res.* 2002 1(1):79-87.

Wendling et al. "Retinoid signaling is essential for patterning the endoderm of the third and fourth pharyngeal arches." *Development.* 2000;127(8):1553-62.

Zantek et al. "MCF-10A-NeoST: A New Cell System for Studying Cell-ECM and Cell-Cell Interactions in Breast Cancer" *Clinical Cancer Research* 2001;7:3640-3648.

Zelinski et al. "Estrogen and Myc Negatively Regulate Expression of the EphA2 Tyrosine Kinase" *Journal of Cellular Biology* 2002;85:714-720.

Zhang et al., "Relative malignant potential of human breast carcinoma cell lines established from pleural effusions and a brain metastasis," *Invasion Metastasis*, 1991;11:204-215.

Zhong et al., "Rho-stimulated contractility contributes to the fibroblastic phenotype of ras-transformed epithelial cells," *Mol. Biol. Cell.*, 1997; 8:2329-2344.

Zisch et al., "Complex formation between EphB2 and Src requires phosphorylation of tyrosine 611 in the EphB2 juxtamembrane region," *Oncogene*, 1998;16:2657-2670.

Zoller et al., "Olgonucleotide-directed mutagenesis using M13-derived vectors: an efficient and general procedure for the production of point mutations in any fragment of DNA," *Nucl. Acids Res.*, 1982; 10:6487-6500.

Becker et al. "Characterization of the SEK-1 receptor tyrosine kinase" *FEBS Letters* 1995;368(2):353-357.

Fox et al. "cDNA cloning and tissue distribution of five human Eph-like receptor protein tyrosine kinases" *Oncogene* 1995;10(5):897-905.

Martone et al. "Immunolocalization of the receptor tyrosine kinase EphA4 in the adult rat central nervous system" *Brain Res.* 1997;771(2):238-250.

McBride et al. "Ephrin-A1 is expressed at sites of vascular development in the mouse," *Mech. Dev.* 1998;77(2):201-204. Abstract only.

Ohta et al. The receptor tyrosine kinase, Cek8, is transiently expressed on subtypes of motoneurons in the spinal cord during development' *Mechanisms Devel.* 1996;54(1):59-69.

Scully et al. "Isolation and characterization of Desk, a Drosophila eph receptor protein tyrosine kinase," *Mol. Cell. Neuro.* 1999;13(5):337-347.

Wada et al. "Glycosylphosphatidylinositol-anchored cell surface proteins regulate position-specific cell affinity in the limb bud" *Devel. Biol.* 1998;202(2):244-252.

* cited by examiner

EPHA2 AS A DIAGNOSTIC TARGET FOR METASTATIC CANCER

RELATED APPLICATIONS

This application claims priority under 35 U.S.C. § 119(e) to U.S. Provisional Application No. 60/149,259, filed Aug. 17, 1999, which is expressly incorporated by reference herein.

GOVERNMENT FUNDING

The present invention was made with government support under Grant No. DAMD 17-98-1-8146, awarded by Army Breast Cancer. The Government has certain rights in this invention.

FIELD OF THE INVENTION

The present invention relates to diagnosis of metastatic disease. More particularly, this invention relates to reagents that can detect a specific epithelial cell tyrosine kinase that is overexpressed in metastatic tumor cells. Most particularly, this invention relates to reagents which bind the epithelial cell tyrosine kinase, and the use of these reagents for cancer diagnosis.

BACKGROUND AND SUMMARY OF THE INVENTION

Cancer cell metastasis requires cellular capacity to 1) detach from a primary tumor, 2) migrate and invade through local tissues, 3) translocate to distant sites in the body (via lymph or blood), 4) colonize a foreign site, and 5) grow and survive in this foreign environment. All of these behaviors are linked to cell adhesions. Cell adhesions control the physical interactions of cells with their microenvironment. Cell adhesions also initiate signals that dictate tumor cell growth, death, and differentiation.

Various cancer cells, including breast cancer cells, are known to exhibit altered cell adhesion. As compared to normal breast epithelia, transformed human breast epithelial cells have decreased cell—cell contacts and increased interactions with the surrounding extracellular matrix. These changes facilitate increased detachment and migration of cancer cells away from cell colonies and are directly linked with alteration in tyrosine phosphorylation of cell membrane proteins. Tyrosine phosphorylation is a potent form of cell signal transduction, and alteration in levels of tyrosine phosphorylation is believed to be important for tumor cell invasiveness. Thus, regulation of tyrosine phosphorylation represents a promising target for therapeutic intervention against metastatic cancer. Tyrosine phosphorylation is controlled by cell membrane tyrosine kinases, and increased expression of tyrosine kinases is known to occur in metastatic cancer cells.

Identification of increase expression of cell membrane tyrosine kinases would aid in the diagnosis and treatment of metastatic diseases. One such tyrosine kinase in EphA2. A member of the Eph family of tyrosine kinases known as Ephrins, EphA2 is a transmembrane receptor tyrosine kinase with a cell-bound ligand. Although cloned a decade ago, see Lindberg, R. A. and Hunter, T., "cDNA Cloning and Characterization of Eck, an Epithelial Cell Receptor Protein-tyrosine Kinase in the Eph/elk Family of Protein Kinases," Mol, Cell. Biol. 10(12), 6316–6324 (1990), rather little is known about EphA2 function.

To facilitate research on EphA2, an improved method for generating a panel of monoclonal antibodies specific for tyrosine phosphorylated proteins has been developed. Using this method, a multiplicity of EphA2 recognizing monoclonal antibodies has been generated. These antibodies have been used to show that EphA2 is overexpressed in metastatic breast, lung, colon, and prostate cells. Because EphA2 is expressed differently in normal and metastatic cells, EphA2-specific antibodies are useful in the diagnosis of metastatic disease. Antibodies produced by one particular hybridoma recognize an intracellular epitope of EphA2 and have been shown to be highly specific in binding to EphA2.

Thus, one aspect of this invention is a compound which specifically binds to an intracellular epitope of EphA2. In a preferred embodiment, the compound is an antibody specific for a domain of the EphA2 protein. However, natural or artificial ligands, peptides, anti-sense, ATP analogues, or other small molecules capable of specifically targeting EphA2 may be employed. A second aspect of this invention is a method for generating antibodies which recognize EphA2 intracellular epitopes. Another aspect of this invention is the use of EphA2-specific antibodies in the diagnosis of metastatic disease. An additional aspect of this invention is a diagnostic reagent specific for detecting EphA2, any fragment thereof, or DNA or RNA coding for the EphA2 protein.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIGS. 1A–C show a series of western blots showing EphA2 expression in cell lines derived from human prostate cells;

FIGS. 3A–B shows EphA2 localization in the cell membranes of various mammary epithelial cell lines, as seen by immunofluorescence microscopy;

DETAILED DESCRIPTION OF THE INVENTION

Antibodies specific for EphA2 have been isolated through an improved method. The method employed is designed for increased sensitivity and diversity of responding hybridomas. According to this method, tyrosine phosphorylated proteins from Ras-transformed human epithelial cells are isolated by affinity chromatography using existing phosphotyrosine-specific antibodies. The tyrosine phosphorylated proteins are then used as an immunogen for producing monoclonal antibodies. Low-dose amounts of tyrosine phosphorylated proteins are injected proximal to lymph nodes, every other day, over a ten day period (the RIMMS strategy). B cells from engorged lymph nodes are then isolated and fused with a Bcl-2-overexpressing myeloma, to minimize apoptosis after fusion. This method results in increased diversity, specificity, and cost-effectiveness of hybridoma production. The hybridomas are first screened to identify those hybridomas producing antibodies capable of distinguishing malignant from normal cancer cells. To date, at least 450 such hybridomas have been identified.

Hybridomas which are specific to EphA2 have been selected. Use of the RIMMS strategy has resulted in the production of various monoclonal antibodies that specifically bind EphA2. Of the first four hybridomas characterized, two recognize independent epitopes on EphA2. The first, D7, recognizes an intracellular epitope. The second, B2D6, binds to an extracellular epitope. D7 has proven to be highly specific for an intracellular epitope of EphA2 and this specificity provides much of the current basis for diagnosis of metastatic tumors. Hybridoma D7, identified as "murine hybridoma D7," was deposited with the American Type Culture Collection (ATCC), 10801 University Blvd., Manassas, Va., 20110-2209, USA, on Dec. 8, 2000, and assigned ATCC number PTA 2755. Hybridoma B2D6, identified as "murine hybridoma B2D6," was deposited with the American Type Culture Collection (ATCC), 10801 University Blvd., Manassas, Va., 20110-2209, USA, on Dec. 8, 2000, and assigned ATCC number PTA 2754.

It is known in the art to use antibodies to detect the presence or overexpression of a specific protein. Because EphA2 is overexpressed in metastatic cells, EphA2-specific antibodies of this invention may be used to detect this overexpression and, thus, to detect metastatic disease. Such techniques include but are not limited to western blotting, dot blotting, precipitation, agglutination, ELISA assays, immunohistochemistry, in situ hybridization, flow cytometry on a variety of tissues or bodily fluids, and a variety of sandwich assays. These techniques are well known in the art. See, for example, U.S. Pat. No. 5,876,949, hereby incorporated by reference. When antibodies specific for an intracellular epitope of EphA2 are used, the cells must be lysed and incubated with the antibody. The above techniques may be performed on whole-cell lysates, or EphA2 may be separated out for testing, such as by immunoprecipitation. The D7 antibodies of this invention are highly specific for an intracellular epitope of EphA2 and have proven to be sensitive to differential expression of EphA2 in metastatic cells. Other techniques, such as immunohistological staining, require whole cells, and may further require cell layers of a particular cell density. Such tests require an antibody specific for an extracellular epitope of EphA2.

The antibodies of this invention may be used to detect metastatic disease in a wide variety of tissue samples. For instance, research using EphA2-specific antibodies has revealed that altered EphA2 expression occurs in breast, kidney, prostate, lung, and colon cells, and it is believed that altered EphA2 expression occurs in other types of cell metastasis, particularly epithelial malignancies. EphA2-specific antibodies may be used to detect metastasis in biopsied tumor tissue. Also, samples of a variety of body fluid samples, such as blood, plasma, spinal fluid, saliva, and urine, can be tested with the antibodies of the present invention. Altered EphA2 expression in these samples indicates the presence of metastatic disease.

Additionally, other antibodies may be used in combination with the antibodies of the present invention to provide further information concerning metastatic disease state. For example, the EphA2 of metastatic cells exhibits altered tyrosine phosphorylation. In normal breast epithelial cells, EphA2 is expressed and is tyrosine phosphorylated. However, in metastatic breast epithelial cells, EphA2 is overexpressed, and the EphA2 is not tyrosine phosphorylated. Because a test quantifying EphA2 expression sometimes may lead to an ambiguous result, it may be desirable to determine tyrosine phosphorylation, as well as the magnitude of EphA2 expression. Thus, a method of diagnosis using the antibodies of this invention in combination with phosphotyrosine-specific antibodies provides data for determining the state of metastatic disease.

Moreover, the EphA2-specific antibodies of this invention can be exploited to detect changes in EphA2 localization which are associated with metastasis. In normal breast and prostate epithelial cells, EphA2 is enriched in within sites of cell adhesion. Conversely, in metastatic prostate cells EphA2 is diffusely distributed, and in metastatic breast cancer cells EphA2 is redistributed into the membrane ruffles. Techniques such as immunohistological staining or immunofluorescent microscopy are well known in the art and may be used to visualize EphA2 distribution. See, for example, U.S. Pat. No. 5,514,554, hereby incorporated by reference. EphA2 expression can be detected by using antibodies capable of detecting whole EphA2 or fragments of the EphA2 protein. Other methods of detecting altered EphA2 expression include detecting DNA or RNA sequences coding for the EphA2 protein.

In order to detect overexpression or altered distribution of EphA2, the EphA2-specific antibodies may be labeled covalently or non-covalently with any of a number of known detectable labels, such fluorescent, radioactive, or enzymatic substances, as is known in the art. Alternatively, a secondary antibody specific for the antibodies of this invention is labeled with a known detectable label and used to detect the EphA2-specific antibodies in the above techniques.

Preferred labels include chromogenic dyes. Among the most commonly used are 3-amino-9-ethylcarbazole (AEC) and 3,3'-diaminobenzidine tetrahydrocholoride (DAB). These can be detected using light microscopy. Also preferred are fluorescent labels. Among the most commonly used fluorescent labeling compounds are fluorescein isothiocyanate, rhodamine, phycoerythrin, phycocyanin, allophycocyanin, o-phthaldehyde and fluorescamine. Chemiluminescent and bioluminescent compounds such as luminol, isoluminol, theromatic acridinium ester, imidazole, acridinium salt, oxalate ester, luciferin, luciferase, and aequorin also may be used. When the fluorescent-labeled antibody is exposed to light of the proper wavelength, its presence can be detected due to its fluorescence.

Also preferred are radioactive labels. Radioactive isotopes which are particularly useful for labeling the antibodies of the present invention include $^{3}H$, $^{125}I$, $^{131}I$, $^{35}S$, $^{32}P$, and $^{14}C$. The radioactive isotope can be detected by such means as the use of a gamma counter, a scintillation counter, or by autoradiography.

Another method in which the antibodies can be detectably labeled is by linking the antibodies to an enzyme and subsequently using the antibodies in an enzyme immunoassay (EIA) or enzyme-linked immunosorbent assay (ELISA). The enzyme, when subsequently exposed to its substrate, reacts with the substrate and generates a chemical moiety which can be detected, for example, by spectrophotometric, fluorometric, or visual means. Enzymes which can be used to detectably label antibodies include, but are not limited to malate dehydrogenase, staphylococcal nuclease, delta-5- steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, and acetylcholinesterase. Other methods of labeling and detecting antibodies are known in the art and are within the scope of this invention.

EXAMPLE 1

Figure 1A:
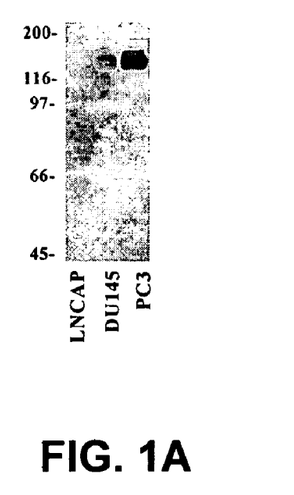
FIG. 1A is a western blot showing EphA2 expression in various human prostate cancer cell lines.

The antibodies produced by the D7 hybridoma are used to detect differential expression of EphA2 between normal prostate epithelial cells and metastatic cells. FIG. 1 shows EphA2 expression in various human prostate cell lines. Referring first to FIG. 1A, three metastatic cell lines, LNCAP, DU145, and PC3, are tested for levels of EphA2 expression. It is known that, of these three cell lines, LNCAP is the least invasive, DU145 is somewhat more invasive, and PC3 is the most invasive. EphA2 expression is determined by western blotting with D7 antibodies. As can be seen in FIG. 1A, EphA2 expression positively correlates with invasiveness.

Figure 1B:
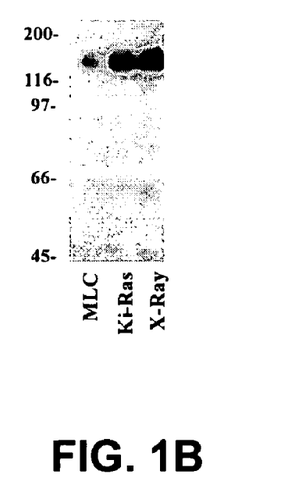
FIG. 1B is a western blot showing EphA2 expression in human prostatic epithelial cell line MLC and expression in that cell line after transformation by oncogenic K-Ras or X-irradiation.
Figure 1C:
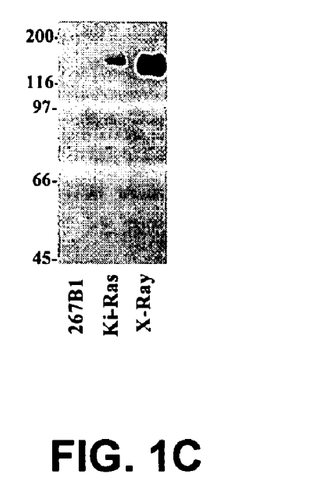
FIG. 1C is similar to FIG. 1B, except showing expression in human prostatic epithelial cell line 267B1 and expression in that cell line after transformation by oncogenic K-Ras or X-irradiation.

In FIG. 1B, D7 antibodies are used to test EphA2 expression in normal MLC cells as compared to expression in transformed cells. Normal MLC cells, MLC cells which have been transformed by K-Ras, and MLC cells with have been transformed by X-irradiation are studied. As can be seen in FIG. 1B, EphA2 is overexpressed in both of the transformed cell lines. FIG. 1C shows results similar to FIG. 1B, except the normal cell line is 267B1. As with FIG. 1B, FIG. 1C shows that EphA2 is overexpressed in the transformed cells. In sum, FIG. 1 demonstrates that EphA2-specific antibodies detect changes in metastatic cells, and that tests using these antibodies indicate the level of metastatic invasiveness.

EXAMPLE 2

Figure 2:
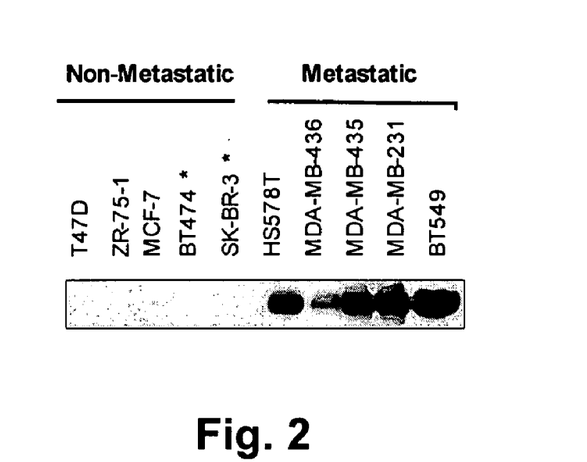
FIG. 2 is a western blot showing EphA2 expression in various human mammary epithelial cell lines.

EphA2 antibodies are used to detect altered EphA2 expression in metastatic mammary cells. EphA2 is expressed in normal mammary epithelial cells. FIG. 2 illustrates altered EphA2 expression in mammary tumor cell lines. As can be seen in FIG. 2, western blots from whole cell lysates using D7 antibodies reveal that EphA2 expression is completely absent in cells derived from non-metastatic breast tumors (ZR75-1, BT474, SKBR3, MDA-MB-435). By contrast, EphA2 is overexpressed in metastatic breast cancer cell lines (MDA-MB-435, MDA-MB-231). Thus, EphA2 antibodies detect altered EphA2 expression in breast cancer cells, which can be used to diagnose metastasis. Moreover, in non-metastatic breast epithelial cells, loss of EphA2 occurs early in the disease, and testing with EphA2-specific antibodies provide information relevant to invasiveness even when other known markers remain normal. Thus, D7 antibodies are useful as a diagnostic, even in early stages of disease.

EXAMPLE 3

EphA2 antibodies in combination with other antibodies are used to detect further alterations in EphA2 expression. As discussed above in Example 2, western blots using D7 can distinguish between non-metastatic and metastatic tumors, with non-metastatic tumors failing to express EphA2, and metastatic cells overexpressing EphA2. However, different results are found when tyrosine phosphorylation is studied. Using a phosphotyrosine-specific antibody, it has been found that EphA2 is phosphorylated in normal cells, but it is not phosphorylated in metastatic cells. Thus, while EphA2 specific antibodies can qualitatively detect a difference between metastatic and non-metastatic mammary tumor cells, diagnostics incorporating both an EphA2-specific antibody and a phosphotyrosine-specific antibody provides a sensitive test for distinguishing between normal, non-metastatic, and metastatic mammary cells.

EXAMPLE 4

Figure 3A:
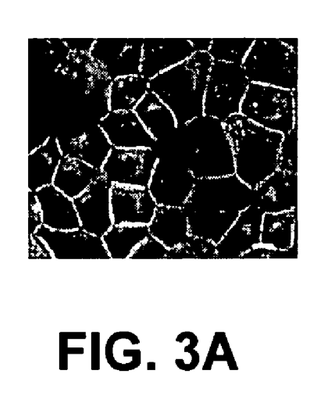
FIG. 3A shows EphA2 localization in sites of cell adhesion in normal MCF-10A cells.
Figure 3B:
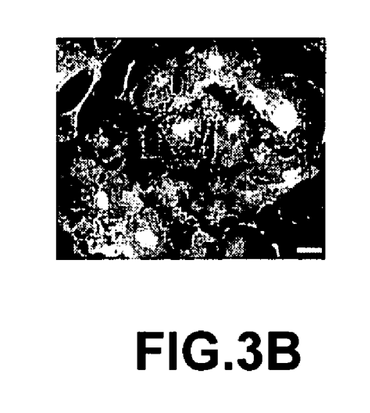
FIG. 3B shows EphA2 redistribution in malignant cells.

Immunofluorescently labeled EphA2-specific antibodies detect redistribution of EphA2 expression in transformed cells. The EphA2-specific antibodies used in this example are produced by a cell line known as B2D6, and these antibodies are specific for an extracellular epitope of EphA2. As seen in FIG. 3A, immunofluorescence with B2D6 demonstrates that EphA2 is found within sites of cell—cell contact in normal cells. However, in transformed cells, shown in FIG. 3B, EphA2 is redistributed. Furthermore, in metastatic cells EphA2 is found in the membrane ruffles. Similarly, in normal prostate epithelial cells, EphA2 is found within sites of cell—cell adhesion, but in metastatic prostate epithelial cells, EphA2 is overexpressed and the expression is diffusely distributed. Therefore, immunofluorescence using EphA2-specific antibodies provides an additional means for diagnosing the transformation and metastatic state of tumor cells.

As shown in Examples 1–4, overexpression, redistribution, and phosphorylation of EphA2 in metastatic cells provide various bases for diagnosis of metastatic tumors using EphA2-specific antibodies. Immunohistochemistry or Western blotting may be used to monitor the change of EphA2 expression in biopsied samples of patient breast tissue, prostate tissue, or tissue from other tumors. Additionally, D7 and other EphA2-specific antibodies can be used to monitor plasma, urine, and other body fluids to detect altered expression of EphA2, which would signal metastasis. Detection of altered tyrosine phosphorylation of EphA2 in combination with information concerning an alteration of EphA2 expression further aids in diagnosis of metastatic disease.

Although the invention has been described in detail with reference to preferred embodiments, variations and modifications exist within the scope and spirit of the invention as described and defined in the following claims.

What is claimed is:

1. A method for detecting the presence of metastatic cells in a cell population comprising the steps of:
   lysing at least a portion of the cell population,
   incubating the lysed cells with a monoclonal antibody that specifically binds EphA2 to allow antibody binding to EphA2, and
   detecting antibody-EphA2 binding;
   wherein the cell population comprises cancer cells selected from the group consisting of breast cancer cells, kidney cancer cells, prostate cancer cells, lung cancer cells, colon cancer cells and epithelial cancer cells; and wherein antibody-EphA2 binding is indicative of the presence of metastatic cells in the cell population.

2. The method claim 1 wherein the antibody binds to an intracellular epitope of EphA2.

3. The method of claim 2 wherein the antibody is produced by hybridoma cell line D7 (ATCC number PTA 2755).

4. The method of claim 1 wherein the antibody is labeled with a detectable label, and the detecting step includes detecting the label.

5. The method of claim 4 wherein the antibody is labeled with a fluorescent label and the detecting step comprises detecting the fluorescent label.

6. The method of claim 4 wherein the antibody is labeled with a radioactive label and the detecting step comprises detecting the radioactive label.

7. The method of claim 1 wherein the cell population comprises cells from a breast or prostate tissue biopsy.

8. The method of claim 1 wherein the cell population is harvested from a body fluid selected from the group consisting of blood, spinal fluid, and urine.

9. The method of claim 8 wherein the detecting step includes a diagnostic method selected from the group consisting of ELISA assays and flow cytometry.

10. The method of claim 1 wherein the incubating and detecting steps comprise western blotting methodology.

11. The method of claim 10 further comprising the steps of
providing a second antibody having phosphotyrosine specificity, and
western blotting with the second antibody.

12. The method of claim 1 wherein the metastatic cells are selected from the group consisting of breast, prostate, lung, and colon cancers.

13. The method of claim 4 wherein the antibody comprises at least one of a fluorescent label, a chemiluminescent label, a bioluminescent label, an enzymatic label, a chromogenic label and a radiolabel, wherein detecting antibody-EphA2 binding comprises detecting at least one detectable label.

14. The method of claim 1 wherein the cell population comprises cells selected from the group consisting of breast cancer cells, kidney cancer cells, prostate cancer cells, lung cancer cells and colon cancer cells.

15. The method of claim 1 wherein the cell population comprises epithelial cancer cells.

16. The method of claim 1 wherein the cell population comprises cells from a tissue biopsy.

17. The method of claim 16 wherein the tissue comprises breast tissue or prostate tissue.

18. The method of claim 1 wherein the cell population comprises cells from a body fluid.

19. The method of claim 18 wherein the body fluid is selected from the group consisting of blood, plasma, spinal fluid, and urine.

20. The method of claim 1 wherein detecting antibody-EphA2 binding comprises utilizing a diagnostic method selected from the group consisting of an ELISA assay, a Western blot, and flow cytometry.

21. The method of claim 1 wherein detecting antibody-EphA2 binding comprises utilizing a Western blot; the method further comprising Western blotting with a second antibody having phosphotyrosine specificity.

22. The method of claim 1 wherein the cell population comprises breast cancer cells.

23. The method of claim 1 wherein the cell population comprises kidney cancer cells.

24. The method of claim 1 wherein the cell population comprises prostate cancer cells.

25. The method of claim 1 wherein the cell population comprises lung cancer cells.

26. The method of claim 1 wherein the cell population comprises colon cancer cells.

27. A method for detecting the presence of metastatic cells in a tissue sample comprising the steps of
incubating the tissue sample with a reagent capable of specific binding to a nucleic acid coding for EphA2 protein, wherein said reagent comprises a nucleic acid that is complementary to the nucleic acid coding for EphA2 protein, to allow reagent binding to the nucleic acid, and
detecting reagent-nucleic acid binding,
wherein the tissue sample comprises cancer cells selected from the group consisting of breast cancer cells, kidney cancer cells, prostate cancer cells, lung cancer cells, colon cancer cells and epithelial cancer cells; and wherein reagent-nucleic acid binding is indicative of the presence of metastatic cells in the tissue sample.

28. The method of claim 27 wherein the nucleic acid coding for EphA2 protein is DNA or RNA.

29. The method of claim 27 further comprising, prior to the detecting step, the step of fixing the cells on a slide, wherein the detecting step comprises detecting the reagent-nucleic acid binding using immunofluorescence staining.

30. A method for detecting the presence of metastatic cells in a cell population comprising:
incubating at least a portion of the cell population with a monoclonal antibody that specifically binds EphA2 to allow binding of the antibody to EphA2; and
detecting antibody-EphA2 binding,
wherein the cell population comprises cancer cells selected from the group consisting of breast cancer cells, kidney cancer cells, prostate cancer cells, lung cancer cells, colon cancer cells and epithelial cancer cells; and wherein antibody-EphA2 binding is indicative of the presence of metastatic cells in the cell population.

31. The method of claim 30 wherein the antibody binds to an intracellular epitope of EphA2.

32. The method of claim 30 wherein the antibody is produced by hybridoma cell line D7 (ATCC number PTA 2755).

33. The method of claim 30 wherein the antibody binds to an extracellular epitope of EphA2.

34. The method of claim of claim 30 wherein antibody-EphA2 binding yields a bound complex comprising a whole cell.

35. The method of claim 34 wherein detecting antibody-EphA2 binding comprises subjecting the bound complex to immunohistochemical staining.

36. The method of claim 30 wherein the antibody is produced by hybridoma cell line B2D6 (ATCC number PTA 2754).

37. The method of claim 30 wherein the bound antibody comprises a detectable label; and wherein detecting antibody-EphA2 binding comprises detecting the label.

38. The method of claim 30 wherein the bound antibody comprises at least one of a fluorescent label, a chemiluminescent label, a bioluminescent label, an enzymatic label, a chromogenic label and a radiolabel; and wherein detecting antibody-EphA2 binding comprises detecting at least one detectable label.

39. The method of claim 30 wherein the cell population comprises cells selected from the group consisting of breast cancer cells, kidney cancer cells, prostate cancer cells, lung cancer cells and colon cancer cells.

40. The method of claim 30 wherein the cell population comprises epithelial cancer cells.

41. The method of claim 30 wherein the cell population comprises metastatic cancer cells.

42. The method of claim 41 wherein the metastatic cells comprise cells selected from the group consisting of breast cancer cells, kidney cancer cells, prostate cancer cells, lung cancer cells, and colon cancer cells.

43. The method of claim 30 wherein the metastatic cells comprise epithelial cancer cells.

44. The method of claim 30 wherein the cell population comprises cells from a tissue biopsy.

45. The method of claim 44 wherein the tissue comprises breast tissue or prostate tissue.

46. The method of claim 30 wherein the cell population comprises cells from a body fluid.

47. The method of claim 46 wherein the body fluid is selected from the group consisting of blood, spinal fluid, and urine.

48. The method of claim 30 wherein detecting antibody-EphA2 binding comprises utilizing a diagnostic method selected from the group consisting of an ELISA assay, a Western blot, and flow cytometry.

49. A method for detecting the presence of cancer cells in a selected cell population comprising:
assaying at least a portion of the selected cell population for at least one of
a change in EphA2 intracellular localization pattern; and
a change in EphA2 phosphorylation content
as compared to the intracellular localization pattern and phosphorylation content in an analogous normal cell population;
wherein the change is indicative of the presence of a cancer cell in the selected cell population.

50. The method of claim 49 wherein a change in intracellular localization pattern or phosphorylation content is indicative of the presence of metastatic cancer cells in the cell population.

51. The method of claim 49 wherein assaying the cell population comprises incubating at least a portion of the selected cell population with a reagent capable of binding to EphA2 to allow binding of the reagent to EphA2; and detecting reagent-EphA2 binding.

52. The method of claim 51 wherein the reagent is an antibody.

53. The method of claim 52 wherein the antibody is produced by hybridoma D7 (ATCC number PTA 2755) or hybridoma B2D6 (ATCC number PTA 2754).

54. A method for determining the disease stage in a cell population comprising cancer cells, the method comprising:
assaying at least a portion of the cell population to determine at least one of
EphA2 intracellular localization pattern; and
EphA2 phosphorylation content; and
wherein the intracellular localization pattern or phosphorylation content is indicative of the disease stage of the cancer cells.

55. The method of claim 54 wherein assaying the cell population comprises incubating at least a portion of the cancer cell population with a reagent capable of binding to EphA2 to allow binding of the reagent to EphA2; and detecting reagent-EphA2 binding.

56. The method of claim 55 wherein the reagent is an antibody.

57. The method of claim 56 wherein the antibody is produced by hybridoma D7 (ATCC number PTA 2755) or hybridoma B2D6 (ATCC number PTA 2754).

58. A method for detecting the presence of cancer cells in a selected cell population comprising:
assaying at least a portion of the selected cell population for at least one of
a change in EphA2 intracellular localization pattern; and
a change in EphA2 phosphorylation content
as compared to the EphA2 intracellular localization pattern and phosphorylation content in an analogous normal cell population; wherein the assaying the cell population comprises incubating at least a portion of the selected cell population with a monoclonal antibody that specifically binds EphA2 to allow antibody binding to EphA2, and wherein the change is indicative of the presence of a cancer cell in the selected cell population.

59. The method of claim 58 further comprising assaying at least a portion of the selected cell population for a change in EphA2 expression level as compared to the EphA2 expression level in an analogous normal cell population, wherein a change in EphA2 expression level is indicative of the presence of nonmetastatic cancer cells in the selected cell population.

60. A method for detecting the presence of metastatic cells in a cell population comprising the steps of:
lysing at least a portion of the cell population;
incubating the lysed cells with an antibody produced by hybridoma D7 (ATCC number PTA 2755) or hybridoma B2D6 (ATCC number PTA 2754) to allow antibody binding to EphA2; and
detecting antibody-EphA2 binding;
wherein antibody-EphA2 binding is indicative of the presence of metastatic cells in the cell population.

61. A method for detecting the presence of metastatic cells in a cell population comprising:
incubating at least a portion of the cell population with an antibody produced by hybridoma D7 (ATCC number PTA 2755) or hybridoma B2D6 (ATCC number PTA 2754) to allow antibody binding to EphA2; and
detecting antibody-EphA2 binding;
wherein antibody-EphA2 binding is indicative of the presence of metastatic cells in the cell population.

62. A method for detecting the presence of cancer cells in a selected cell population comprising:
incubating at least a portion of the selected cell population with an antibody produced by hybridoma D7 (ATCC number PTA 2755) or hybridoma B2D6 (ATCC number PTA 2754) to allow binding of the antibody to EphA2; and
detecting antibody-EphA2 binding so as to detect at least one of
a change in EphA2 intracellular localization pattern; and
a change in EphA2 phosphorylation content
as compared to the intracellular localization pattern and phosphorylation content in an analogous normal cell population; wherein the change is indicative of the presence of a cancer cell in the selected cell population.

63. A method for determining the disease stage in a cell population comprising cancer cells, the method comprising:
incubating at least a portion of the selected cell population with an antibody produced by hybridoma D7 (ATCC number PTA 2755) or hybridoma B2D6 (ATCC number PTA 2754) to allow binding of the antibody to EphA2;
detecting antibody-EphA2 binding so as to detect at least one of
EphA2 intracellular localization; and
EphA2 phosphorylation content; and wherein the intracellular localization pattern or phosphorylation content is indicative of the disease stage of the cancer cells.

64. A method for detecting the presence of cancer cells in a selected cell population comprising:

incubating at least a portion of the selected cell population with an antibody produced by hybridoma D7 (ATCC number PTA 2755) or hybridoma B2D6 (ATCC number PTA 2754) to allow binding of the antibody to EphA2;

detecting antibody-EphA2 binding so as to detect at least one of a change in EphA2 expression level;

a change in EphA2 intracellular localization pattern; and a change in EphA2 phosphorylation content as compared to the EphA2 expression level, intracellular localization pattern and phosphorylation content in an analogous normal cell population; wherein the change is indicative of the presence of a cancer cell in the selected cell population.

* * * * *

UNITED STATES PATENT AND TRADEMARK OFFICE
CERTIFICATE OF CORRECTION

PATENT NO. : 7,192,698 B1
APPLICATION NO. : 09/640952
DATED : March 20, 2007
INVENTOR(S) : Michael S. Kinch et al.

It is certified that error appears in the above-identified patent and that said Letters Patent is hereby corrected as shown below:

On face page, page 6, OTHER PUBLICATIONS
Delete the reference by Stein et al. and replace with -- Stein et al. "Nck recruitment to Eh receptor, EphB1/ELK couples ligand activation to c-JUN kinase," *J. Biol. Chem.* 1998; 273:1303-1308. --;

At column 1, line 57, delete the word "increase" and replace with -- increased --;

At column 1, line 59, delete the word "in" and replace with -- is --;

In claim 19, column 7, line 48, delete "plasma,".

Signed and Sealed this

Thirty-first Day of March, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 7,192,698 B1 |
| APPLICATION NO. | : 09/640952 |
| DATED | : March 20, 2007 |
| INVENTOR(S) | : Michael S. Kinch et al. |

It is certified that error appears in the above-identified patent and that said Letters Patent is hereby corrected as shown below:

Title Page,

(*) Notice: Subject to any disclaimer, the term of this patent is extended or adjusted under 35 U.S.C. 154(b) by 976 days.

should read (*) Notice: Subject to any disclaimer, the term of this patent is extended or adjusted under 35 U.S.C. 154(b) by 943 days.

Signed and Sealed this

Fourth Day of May, 2010

David J. Kappos
*Director of the United States Patent and Trademark Office*